US006598915B2

(12) United States Patent  
Ngo et al.

(10) Patent No.: US 6,598,915 B2  
(45) Date of Patent: Jul. 29, 2003

(54) TOOL FOR LIFTING A TRAY

(76) Inventors: Tri Van Ngo, 9406 N. Compton St., Indianapolis, IN (US) 46240; Jeffrey A. Howerton, 8273 Harcourt Rd. 326-C, Indianapolis, IN (US) 46250; Joe Peyton, 4004 W. 193rd St., Westfield, IN (US) 46074

( * ) Notice: Subject to any disclaimer, the term of this patent is extended or adjusted under 35 U.S.C. 154(b) by 0 days.

(21) Appl. No.: 10/040,527

(22) Filed: Nov. 1, 2001

(65) Prior Publication Data

US 2003/0080574 A1 May 1, 2003

(51) Int. Cl.[7] .................................................. A47J 45/00
(52) U.S. Cl. ....................... 294/27.1; 294/15; 294/26
(58) Field of Search ........................... 294/9–12, 15, 294/25, 26, 27.1–33, 137, 142, 143, 145, 153, 154, 158, 170, 171, 903; 16/110.1, 114.1, 406, 408, 422, 425, 426; 220/759, 769, 770; 229/117.19, 117.21, 117.23, 117.24; D7/394; D9/434, 455; 206/711

(56) References Cited

U.S. PATENT DOCUMENTS

| | | | | | |
|---|---|---|---|---|---|
| 209,889 | A | * | 11/1878 | Harper | 294/26 |
| 254,933 | A | * | 3/1882 | Dee | 294/15 |
| 539,690 | A | * | 5/1895 | Lasher, Jr. | 294/26 |
| 1,079,527 | A | * | 11/1913 | Wallace | 294/137 X |
| 1,540,155 | A | * | 6/1925 | Wydom et al. | 294/170 |
| 1,903,185 | A | * | 3/1933 | Lewis | 220/769 X |
| 1,985,571 | A | * | 12/1934 | Hetzel | 294/26 X |
| 2,271,901 | A | * | 2/1942 | Smith et al. | 294/26 |
| 2,749,172 | A | * | 6/1956 | Jacobs | 294/26 |
| 3,179,287 | A | * | 4/1965 | Rickmeier | 294/27.1 |
| 3,608,945 | A | * | 9/1971 | Heitz | 294/27.1 |
| 3,701,558 | A | * | 10/1972 | Baker | 229/117.19 X |
| 3,939,973 | A | * | 2/1976 | Wallestad | 294/27.1 |
| 4,039,121 | A | * | 8/1977 | Crane | 229/117.19 X |
| 4,165,115 | A | | 8/1979 | Olsson | |
| 4,171,144 | A | | 10/1979 | Rodriguez | |
| 4,190,278 | A | * | 2/1980 | Jancik, Jr. | 294/15 |
| 4,245,763 | A | * | 1/1981 | Weinberg | 294/15 |
| D264,037 | S | | 4/1982 | Johnson | |
| 4,716,025 | A | | 12/1987 | Nichols | |
| D294,559 | S | * | 3/1988 | Schwalbach | 294/137 X |
| D308,457 | S | | 6/1990 | Bleiler | |
| D340,863 | S | * | 11/1993 | Daigle | 294/137 X |
| 5,397,158 | A | * | 3/1995 | Brass et al. | 294/15 |
| 5,436,610 | A | * | 7/1995 | Ballesty et al. | 340/286.02 |
| 5,487,581 | A | * | 1/1996 | Carmo et al. | 294/137 |
| 5,522,116 | A | * | 6/1996 | Enneking et al. | 294/15 |
| D383,971 | S | | 9/1997 | Garfinkle | |
| 5,752,826 | A | | 5/1998 | Andreiko | |
| D402,884 | S | | 12/1998 | Wood | |
| 5,884,996 | A | | 3/1999 | Cottone et al. | |
| D417,393 | S | * | 12/1999 | DiMeo et al. | D9/434 |
| 6,092,670 | A | | 7/2000 | Marriott | |
| 6,176,559 | B1 | * | 1/2001 | Tiramani et al. | 312/108 |
| 6,412,838 | B1 | * | 7/2002 | Malamud | 294/15 |

FOREIGN PATENT DOCUMENTS

| CH | 63992 | * | 2/1913 | 294/27.1 |
|---|---|---|---|---|
| PL | 37408 | * | 3/1955 | 294/15 |

* cited by examiner

Primary Examiner—Eileen D. Lillis  
Assistant Examiner—Paul T. Chin  
(74) Attorney, Agent, or Firm—Maginot, Moore & Bowman

(57) ABSTRACT

A tool for lifting a tray or a vessel having loop or hook handles comprises a substantially planar body having an upper end configured for hand holding and a lower end configured for receiving a handle of the tray or the vessel. The body includes a first hook and a second hook for catching a loop handle. The body may also include an opening disposed close to the lower end for receiving a hook handle. In addition, the body may define a handhold slot configured to fit a hand of the user and reduce slippage. Preferably, the tool is made of disposable material.

17 Claims, 13 Drawing Sheets

TOOL FOR LIFTING A TRAY

BACKGROUND OF THE INVENTION

The present invention relates to a tool for lifting a tray or a vessel used in healthcare or other related industries, specifically a tool for lifting trays containing instruments that have been autoclaved or sterilized by heat. More particularly, the invention concerns a disposable tool for lifting a tray or vessel that has loop or hook handles.

Most instruments used in healthcare practices have to be sterilized prior to use. These instruments usually are placed in trays to be sterilized by steam or autoclaving. Currently, the trays used for sterilization are made of a metal such as stainless steel, and usually have either loop handles or hook handles disposed at each end. Some medical trays have no handles, but will have a flange disposed along the rim of the tray to aid lifting. The flange may be curving downwardly for easier gripping.

After steaming or autoclaving, the trays are handled while they are still hot. The handler may wear protective gloves or safety mitts for protection from the heated trays. However, the gloves or the mitts usually are not sterile because they are reused many times. Therefore, they can be a source of contamination to the sterilized instruments. Although sterile gloves are commercially available, they are not protective against heat.

Tools for lifting hot items have been disclosed in a number of U.S. patents. For instance, U.S. Pat. No. Des. 308,457 shows a lifting handle for a deep fryer basket having a long handle at one end and three hooks at an opposite end. U.S. Pat. No. Des 264,037 shows an oven rack moving tool having a long handle at one end and two branching hooks at the opposite end. U.S. Pat. No. 4,165,115 discloses a jar holder for holding a jar over a heating pan. The jar holder has a long handle and a means for receiving the edge portion at the opening of the jar. These devices are not suitable for lifting hot sterilized medical trays.

A device designed for lifting hot trays has been disclosed in U.S. Pat. No. 4,171,144. This device is constructed with a substantially tubular, insulating handle, and a pair of tines projecting from a forward end of the handle. The separation between the tines, corresponding to the lateral dimension of the tray to be lifted, is adjustable by means of radial slots machined around the periphery of a bezel in the forward end of the handle. To lift a tray, the distance between the tines is set to correspond to the width of the tray below the upper flanges of the tray, and then the radially adjustable tines are fixed in position. The device is inserted with the tines forward under the flanges of the tray. The tray may then be lifted and maneuvered by corresponding movements of the handle portion, which is firmly gripped by the user's hand. The '144 device, however, does not work with a tray that has no flanges.

Another device designed for lifting hot trays is disclosed in U.S. Pat. No. 6,092,670. This device is detachably secured at a corner of a rectangular steam pan and to a flange thereof, whereby the steam pan may be safely removed from the top of a steam table with reduced danger of scalding the person lifting the steam pan. The '670 device comprises a flat, generally triangular-shaped base having a means for gripping the flange of the tray, and a handle disposed upwardly away from the plane of the top of the steam pan. To lift a tray, a pair of the '670 devices is attached at opposing corners of a tray by engaging the gripping means to the flanges of the tray. Similar to the device of '144 patent, the '670 device is limited to use with trays having flanges along the upper rim of the trays.

Further, a few tools specifically designed for lifting medical trays are commercially available. However, these tools usually are made of metal wire, which makes the tools relatively expensive, thus reuse is necessary. In order to reuse the tools, they have to be thoroughly cleaned, packed and sterilized. The process of cleaning, packaging, and sterilization can be costly. The cost includes labor, wrapping material and utilities for cleaning and sterilization.

In addition, some commercial metal wire tools are designed for use with trays having a specific type of handles. A tool intended for use with a tray with loop handles cannot be used with a tray with hook handles and vice versa.

Thus, there is a need for a one-time use, sterile tool for lifting sterilized trays that have either loop or hook handles. The tool should protect against heat, but be compact so that it requires minimal cost for packaging, sterilization, shipping or storage. In general, the tool should be inexpensive to produce and should not require reuse to be cost effective.

There is also a need for a versatile tool that can be used with trays having different types of handles.

SUMMARY OF THE INVENTION

To address these needs, the present invention provides a tool for lifting a tray or a vessel that has loop or hook handles. The tool comprises a substantially planar body having an upper end for handholding and a lower end configured to receive a handle of the tray.

In one embodiment of the present invention, the body defines a first rim and a second rim extending between the upper end and the lower end. Each rim preferably is rigid so to provide strength to the body. Furthermore, each rim defines a hook extending therefrom. The hooks are separated by the lower end of the body by a width corresponding to the width of the interior of a loop handle of a tray or a vessel such that the hooks are capable of catching the loop handle.

In one feature of this embodiment, the lower end may curve substantially along the hooks such that the lower end of the planar body acts as a wide hook. The hook on each rim may protrude substantially from the wide hook.

In another feature, the body defines a handhold slot disposed below the upper end of the body. The handhold slot is configured for easy gripping, and may have a gripping wall with a surface design to prevent slippage. The upper end may further define a support bar extending between said first rim and said second rim for supporting the handhold slot and for gripping.

In another embodiment of the present invention, a tool for lifting comprises a substantially planar body defining an upper end, a lower end, and an opening disposed above the lower end. The opening is configured for receiving a hook handle of a tray or a vessel. The body may further define a support rib disposed immediately below the opening against which the hook handle rests when the tray is lifted.

In this embodiment, the body may define a handhold slot disposed below the upper end and above the opening. The upper end may define a support bar for handholding.

In yet another embodiment of the present invention, a tool for lifting comprises a substantially planar body having an upper end, a lower end, and a first rim and a second rim extending between the upper end and the lower end. The first rim defines a first hook extending therefrom, the second rim defines a second hook extending therefrom, the first and second hooks being separated at the lower end by a width slightly less than the width of the interior of a loop handle of a tray or a vessel. The first and the second hooks are insertable through the loop handle to catch the tray when the tray is lifted.

In a further feature of this embodiment, the body defines an opening configured to receive a hook handle of a tray or a vessel. The opening is disposed above the lower end and may be supported by a rib extending across the body between the first and the second rims. Thus, this embodiment can be used with either type of handle i.e., hook or loop handle.

In one aspect of the present invention, the body may be made of any suitable heat resistant material, most preferably a disposable plastic. The body may be formed as a solid piece or as a strong mesh. Preferably, the body is made of material strong enough to hold the weight of the tray or the vessel with its contents. The tool of the present invention should be able to withstand any suitable method of sterilization.

It is one object of the invention to provide a versatile tool for lifting a tray or a vessel that has either loop or hook handles. The tool can be used for lifting a heated tray or a vessel after a process of sterilization. A further central object is to make a tool that can be sterilized and packaged, and that is most preferably disposable.

One benefit of the invention is that the risk of contamination to the tray or the vessel can be reduced. A further benefit is that the cost of sterilization of instruments used in healthcare and related industries can be reduced. Other objects and benefits of the invention will become apparent upon consideration of the following written description together with the accompanying figures.

DESCRIPTION OF THE PREFERRED EMBODIMENT

Figure 1:
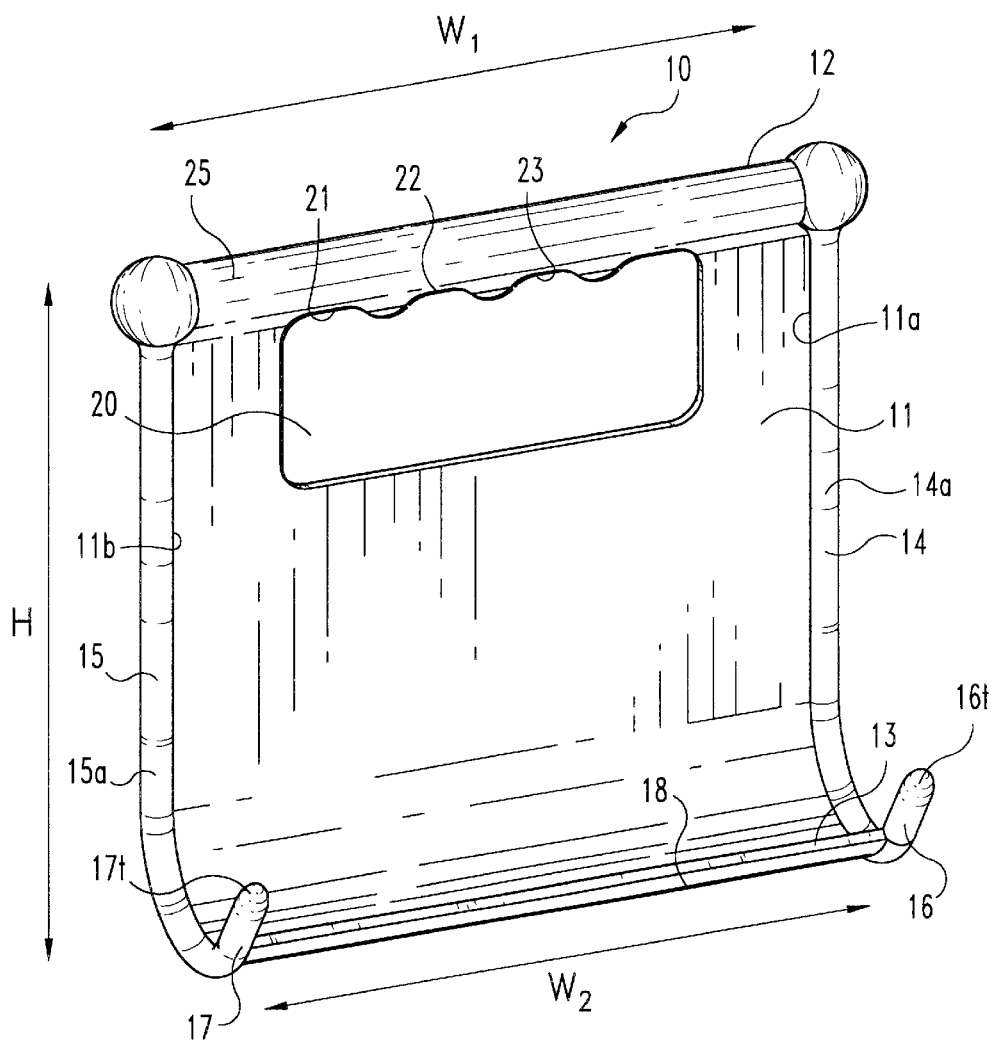
FIG. 1 is a front perspective view of a tool for lifting sterilized tray in accordance with one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended. The invention includes any alterations and further modifications in the illustrated tools and further applications of the principles of the invention, which would normally occur to one skilled in the art to which the invention relates.

The present invention contemplates a tool for lifting a tray, which includes any vessel or any type of structure that has loop, or hook handles. For instance, the inventive lifting tool can be used with JARVIT instrument sterilizing trays or trays offered in V. MUELLER's catalog. The tool may be also used with a tray that has no handles but has flanges along the upper edge of the tray, especially flanges that are curved downwardly for easier gripping.

In one embodiment of the present invention depicted in FIGS. 1–6, a tool 10 comprises a substantially planar body 11 having an upper end 12 and a lower end 13 separated at a height H. The body 11 further defines a first rim 14 and a second rim 15 extending between the upper end 12 and the lower end 13, or along the side edges 11a, 11b of the body 11. The rims 14, 15 are relatively more rigid than the body 11.

In one specific embodiment, the body 11 has an upper width W1 between the rims 14, 15, and a lower width W2 at the lower end 13.

In a preferred embodiment, the first rim 14 defines a first hook 16 and a second rim 15 defines a second hook 17, with both the first and second hooks extending from the lower end 13. The first rim 14 and the second rim 15 may be formed of rods 14a, 15a that provide support to the body 11.

Figure 7:
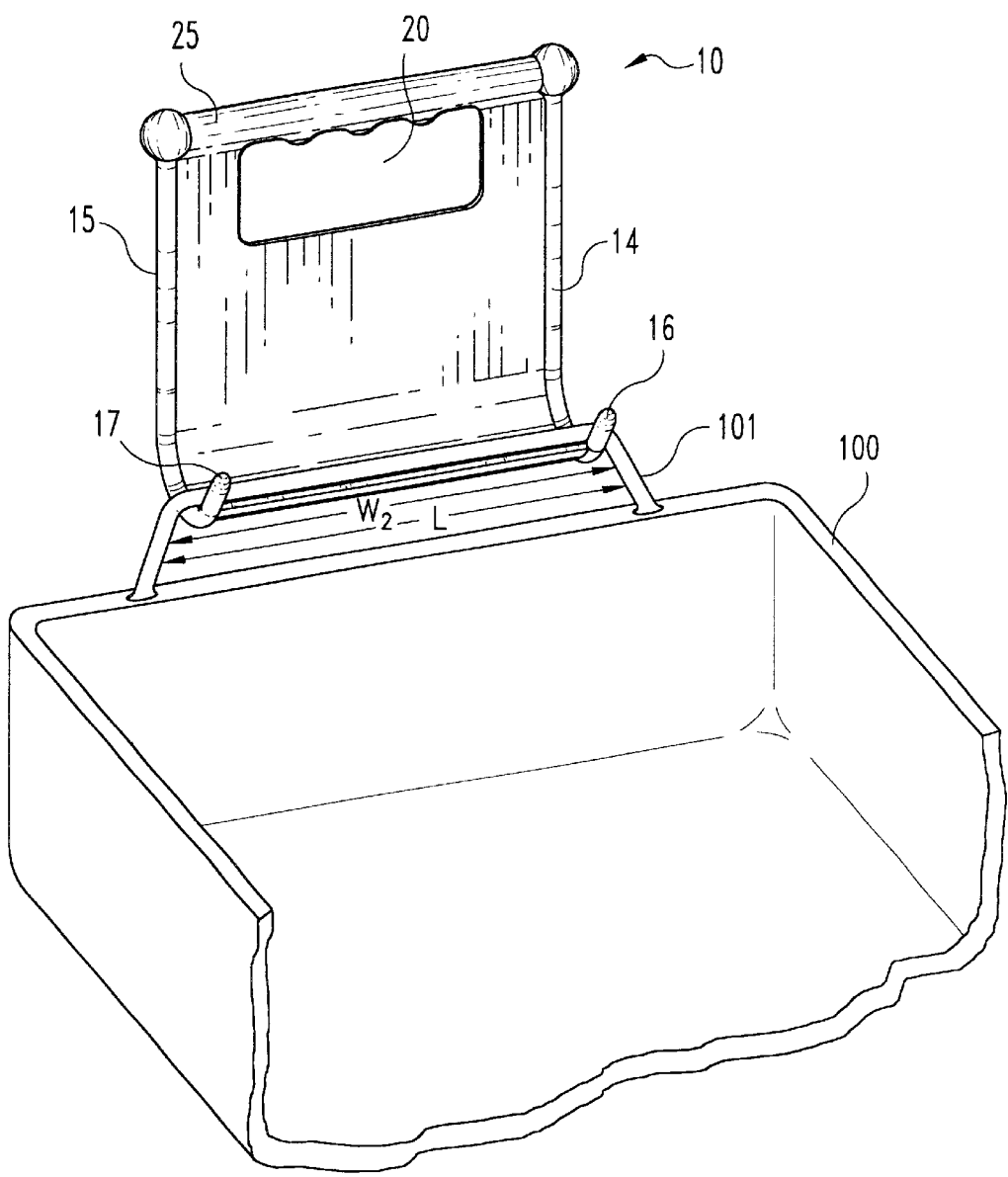
FIG. 7 is a partial perspective view of the tool shown in FIGS. 1–6 shown in position to lift a tray having loop handles.

As demonstrated in FIG. 7, the lower width W2 between the first hook 16 and the second hook 17 should be slightly less than the interior width L of the loop handle 101 of a tray 100. The first hook 16 and the second hook 17 of each tool 10 are insertable through each loop handle 101 of the tray 100. When the user lifts up the tool 10, the first hook 16 and the second hook 17 engage the loop handle 101 of the tray 100.

In another specific embodiment, the height H of the body 11 is substantially equal to or slightly less than the upper width W1, making the body 11 relatively short and compact. The height H and the upper width W1 each should be between 8 to 25 cm. Preferably, the height H and the upper width W1 each is 10 cm.

The lower width W2 may be equal to or slightly less than the upper width W1 so that the body 11 is slightly tapered. Preferably the lower width W2 is less than 10 cm. The tapered body 11 accommodates a wider handgrip at the upper end 12, while it keeps the hooks engagable through the loop handle that has a relatively narrower interior width L. In addition, the tapered body design also reduces the amount of material used in the production of the tool, thus reducing the cost of production.

Figure 3:
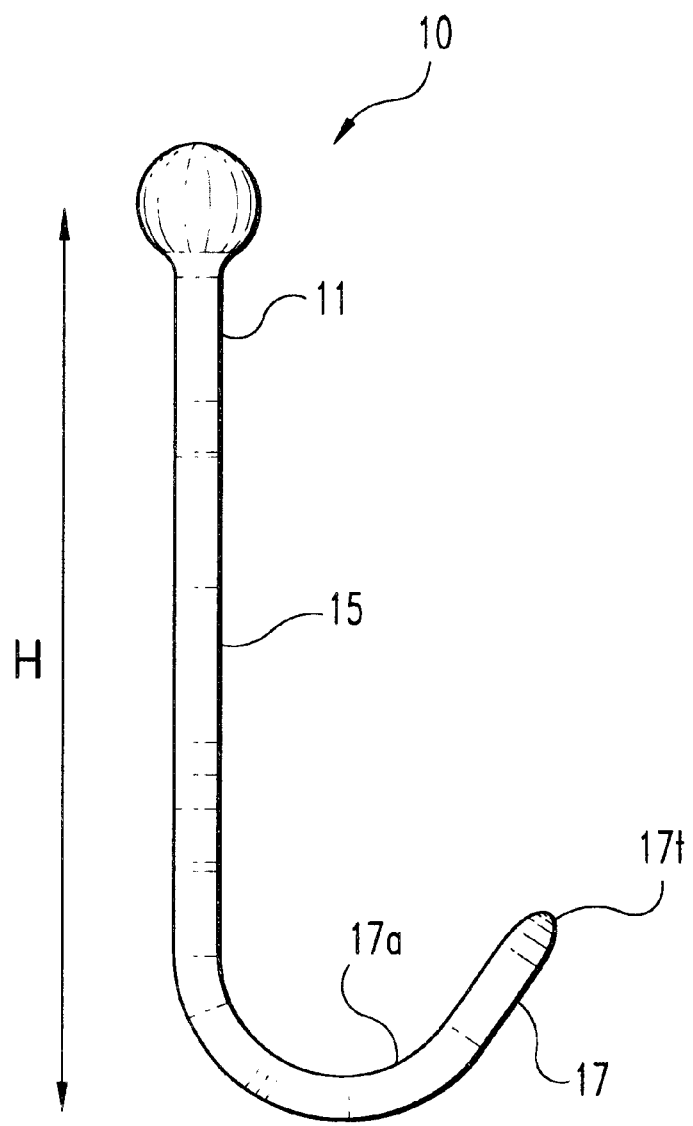
FIG. 3 is a side view of the tool shown in FIGS. 1–2.
Figure 4:
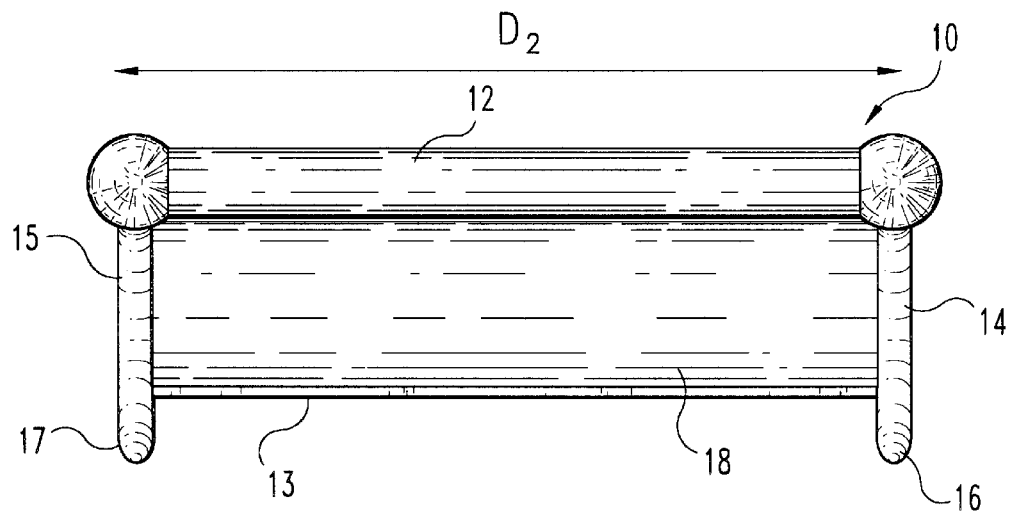
FIG. 4 is a top view of the tool shown in FIGS. 1–3.
Figure 5:
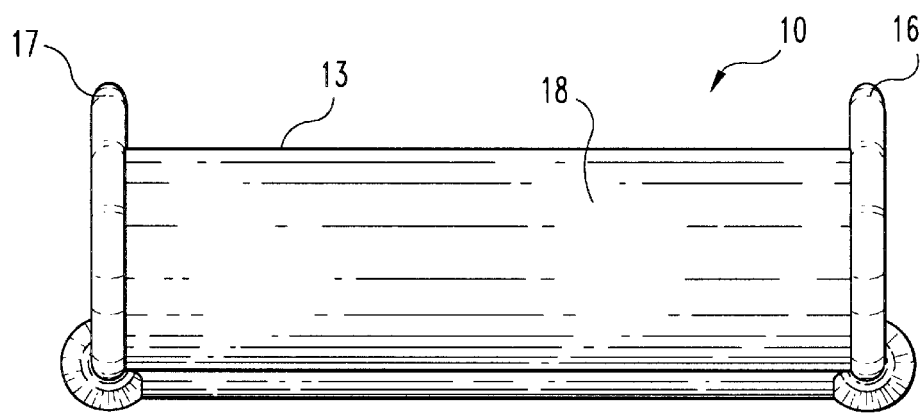
FIG. 5 is a bottom view of the tool shown in FIGS. 1–4.
Figure 6:
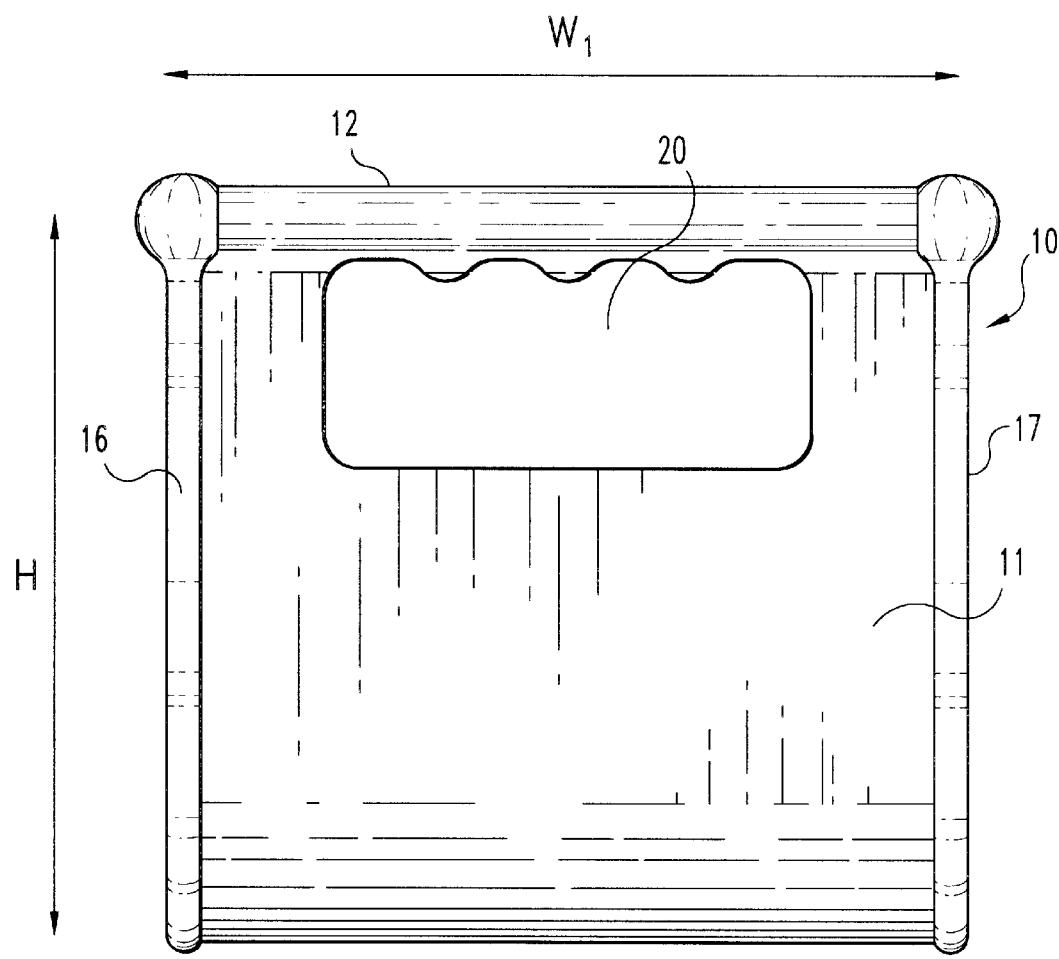
FIG. 6 is a rear view of the tool shown in FIGS. 1–5.

In one feature of the above embodiment, the first hook 16 and the second hook 17 each is suitably curved so that the loop handle 101 is reasonably secured thereon. This curvature, as best seen in FIG. 3, forms a recess 17a that is deep enough for the loop handle to rest in without being accidentally dislodged. In one specific embodiment, the hooks are curved through at least 120 degrees.

As shown in FIG. 1, each of the hooks 16, 17, defines a tip 16t and 17t, respectively. In one specific embodiment (not shown), the tips 16t and 17t are flattened or pointed to facilitate grabbing of the handles that are hingedly attached to the sides of the tray, especially the handles that loosely hang substantially downward and substantially parallel to the side of the tray.

Alternatively, in a case in which the tray has no handle, but has downward flanges along its upper rim (not shown), the first hook 16 and the second hook 17 define suitable curvature for engaging the downward flange of the tray (not shown).

Figure 2:
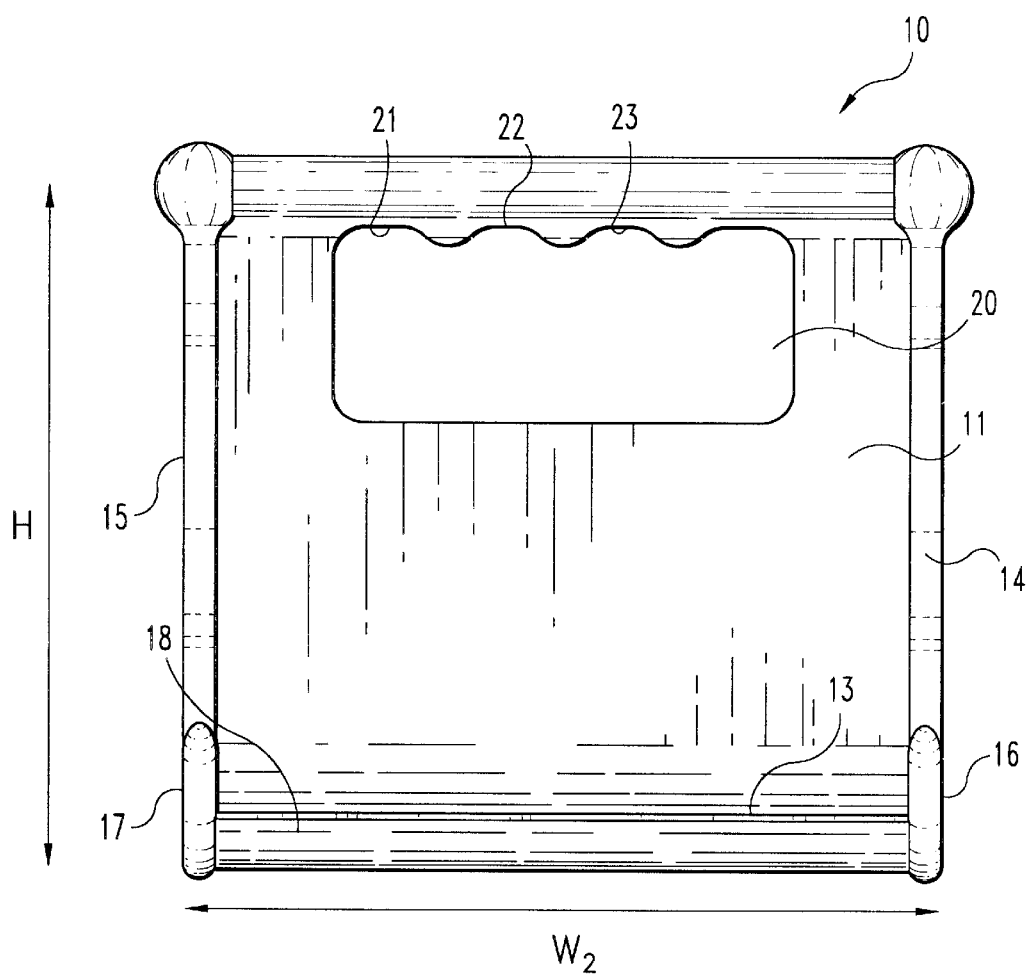
FIG. 2 is a front view of the tool shown in FIG. 1.

Returning to FIGS. 1–6, in another feature of the present embodiment, the body 11 has a lower end 13 that preferably follows the curvature of the hooks 16, 17 such that the lower end 13 forms a wide hook 18. The wide hook 18 strengthens the first hook 16 and the second hook 17. The first hook 16 and the second hook 17 may end flush with the wide hook 18 or may protrude substantially from the wide hook 18 as shown in FIG. 2. The wide hook 18 may be insertable through the loop handle of a tray to help support the tray thereon.

In the preferred embodiment, the body 11 may include a handhold slot 20 disposed slightly below the upper end 12. The handhold slot 20 is sized to receive the four fingers of a hand of a user. A top wall 21 of the handhold slot 20, where the user's fingers grip, may have curves 22 designed for receiving individual fingers. The top wall 21 may further include a surface 23 designed for preventing slippage.

The upper end 12 of the body 11, above the handhold slot 20, is preferably reinforced with a support bar 25 extending from the first rim 14 to the second rim 15, to provide strength to the handhold slot 20 when the tool 10 is lifted. The support bar 25 may be a rounded rod sized for easy gripping.

In another embodiment of the present invention, as illustrated in FIGS. 8–13, a tool 40 comprises a substantially planar body 41 having an upper end 42 and a lower end 43 separated between a height H. The body 40 defines a first rim 44 and a second rim 45 extending between the upper end 42 and the lower end 43. The first rim 44 is separated from the second rim 45 at the upper end 42 at an upper width W1, and at the lower end 43 at a lower width W2. Like in the previous embodiment, the height H is substantially equal to or less than the width W1, whereas the upper width W1 is substantially equal to or more than the lower width W2. The described dimension is beneficial in making the tool compact. The first rim 44 defines a first hook 46 extending from the lower end; the second rim 45 defines a second hook 47 extending from the lower end. Like what has been described herein above, the width W2 should be slightly less than the width of the inner side of the loop handle of a tray. Consequently, the first hook 46 and the second hook 47 should be insertable through the loop handle so that when the user lifts the tool 40, the first hook 46 and the second hook 47 catch the loop handle.

Figure 8:
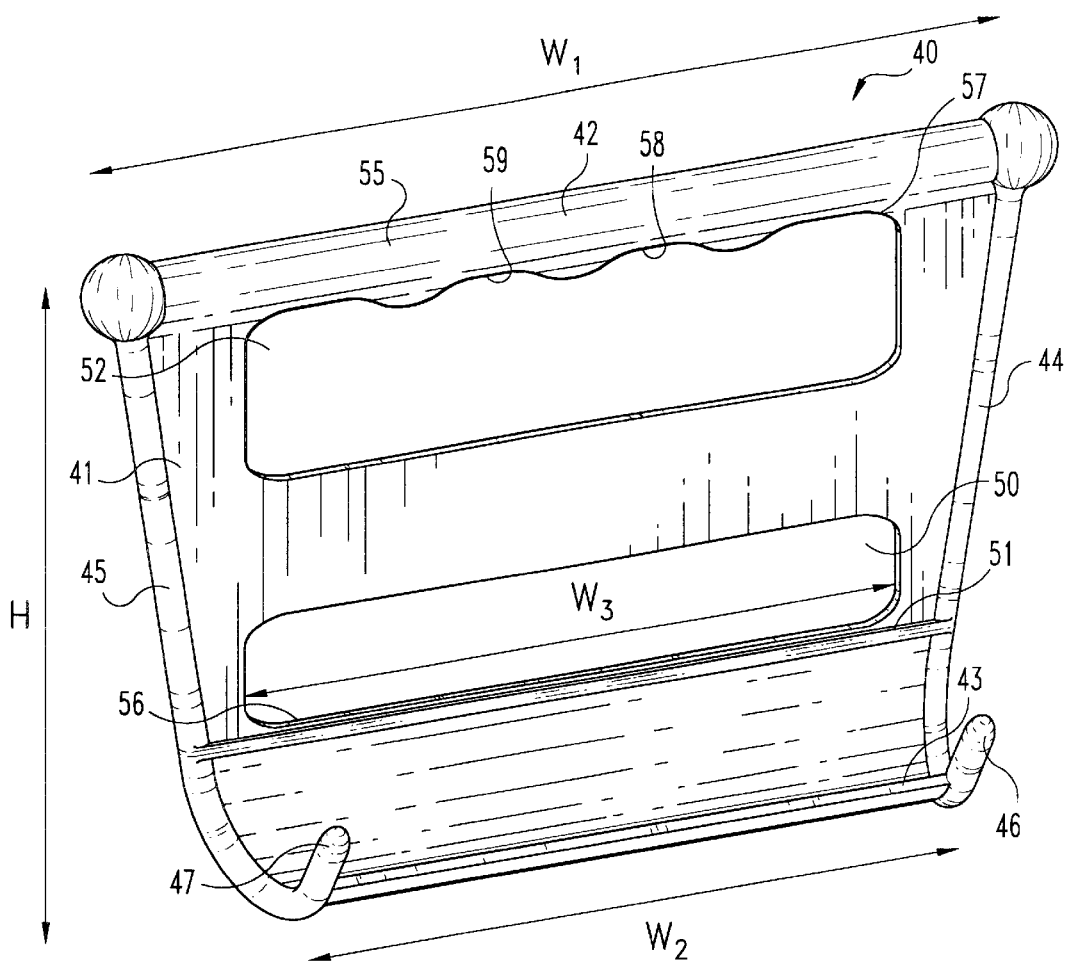
FIG. 8 is a front perspective view of a tool according to another embodiment of the present invention.
Figure 9:
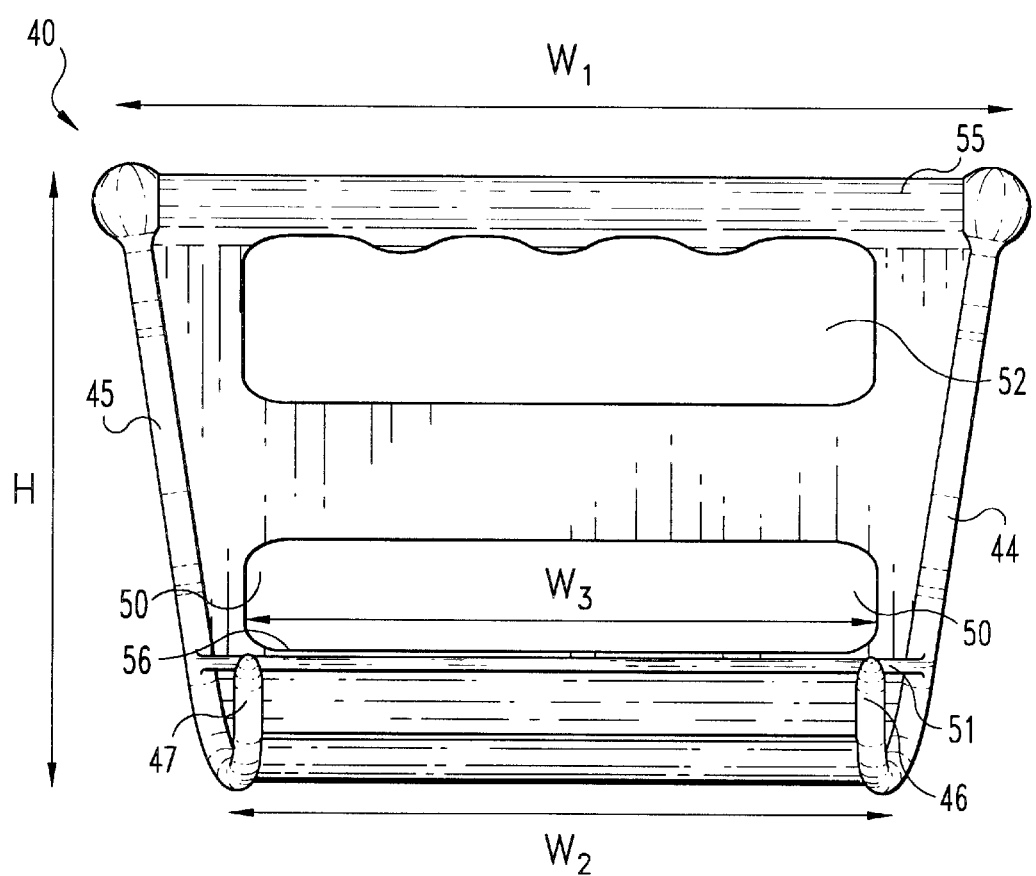
FIG. 9 is a front view of the tool shown in FIG. 8.
Figure 10:
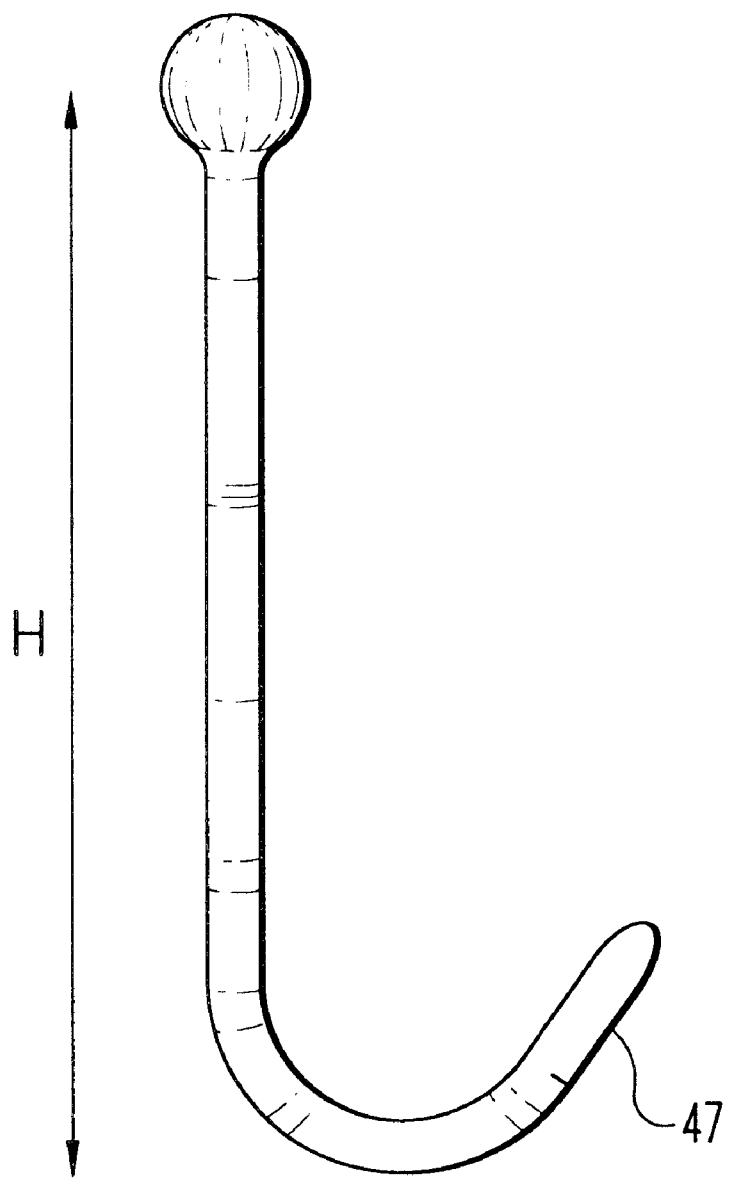
FIG. 10 is a side view of the tool shown in FIGS. 8–9.
Figure 11:
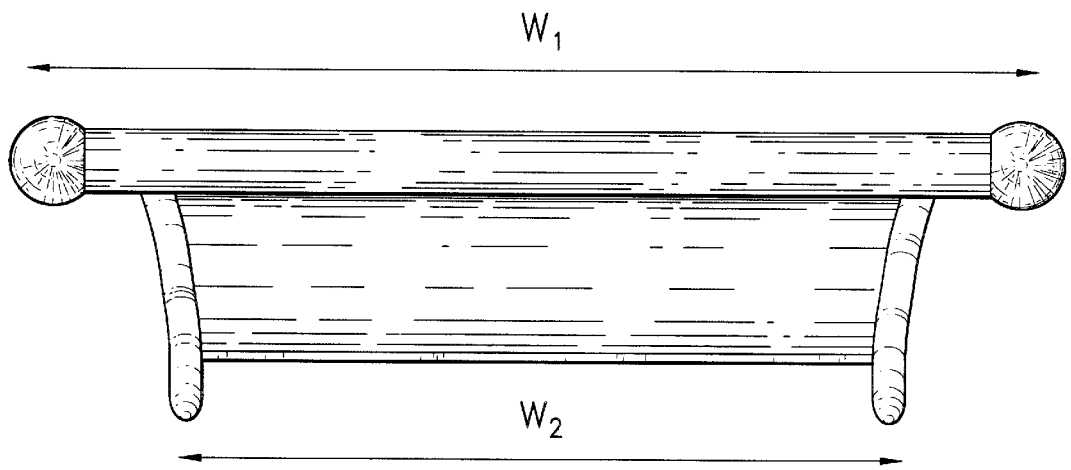
FIG. 11 is a top view of the tool shown in FIGS. 8–10.
Figure 12:
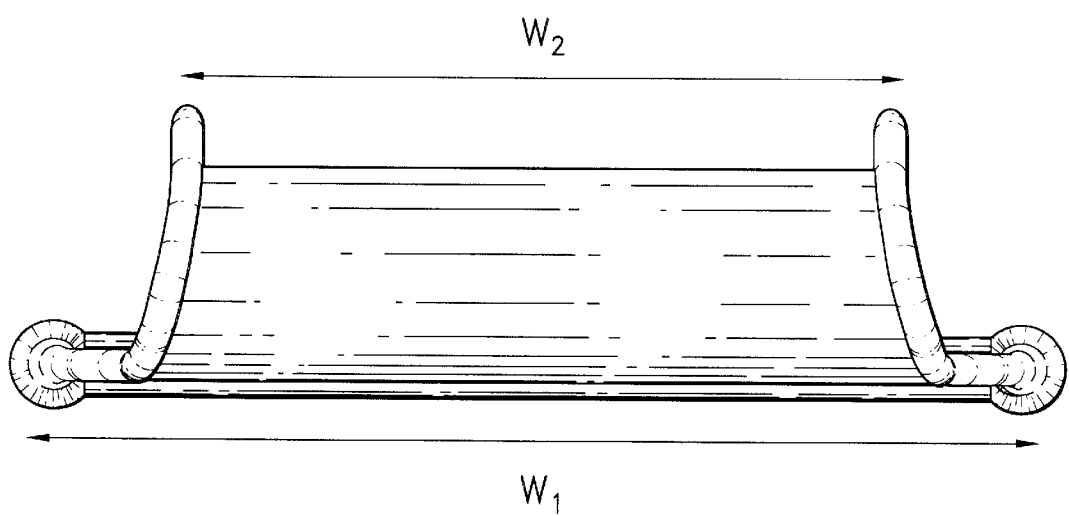
FIG. 12 is a bottom view of the tool shown in FIGS. 8–11.
Figure 13:
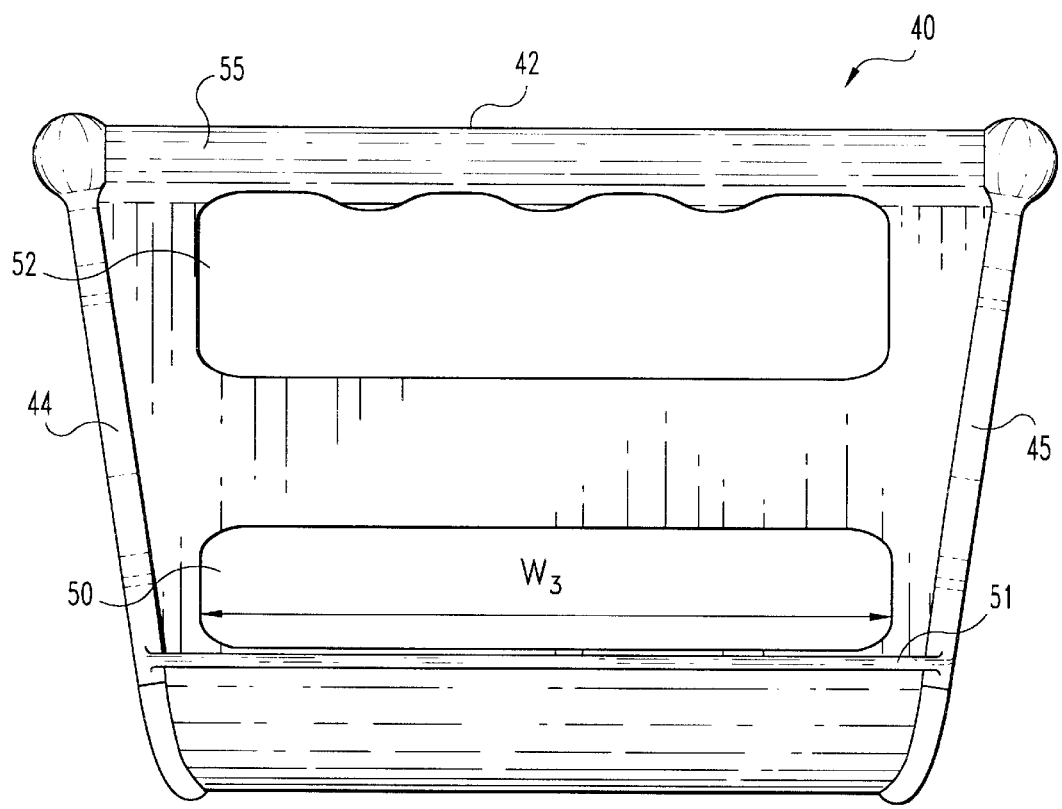
FIG. 13 is a rear view of the tool shown in FIGS. 8–12.

In addition, in this preferred embodiment, the body 41 further defines an opening 50 configured to receive a hook handle of a tray. The opening 50 defines a width W3 that is slightly more than the width of the hook handle. As shown in FIGS. 8, 9 and 13, the opening 50 is disposed close to the lower end 43. Further, the opening 50 defines a rigid lower lip 56 on which the hook handle of the tray rests. The lower lip should be suitably thin whereby the lower lip 56 can be inserted between the hook handle of the tray and the side of the tray to engage the hook handle. The body 41 may define a rigid rib extending between the first rim 44 and the second rim 45 and immediately disposed below the lower lip 56 to provide further support for the handle.

Further in this embodiment, the body 41 may include a handhold slot 52 disposed close to the upper end 42 and above the opening 50. Preferably, the upper end 42 is rigid or sufficiently reinforced with a support bar 55 for strength. Like the handhold slot in the previous embodiment, the handhold slot 52 may define an upper wall 57 defining curves 58 for receiving four fingers of the user. The upper wall 57 may also include a surface 59 designed to prevent slippage.

As shown in FIGS. 8, 9 and 13, and as eluded to above, the body 41 may be tapered such that the upper width W1 of the upper end 42 is wider than the lower width W2 of the lower end 43. The upper width W1 of the upper end 42 is wide enough to position the handhold slot 52 therebelow. The lower width W2 at the lower end 43 corresponds to the inner width of the loop handle of the tray, allowing the first hook 46 and the second hook 47 to be insertable through the loop handle.

Figure 14:
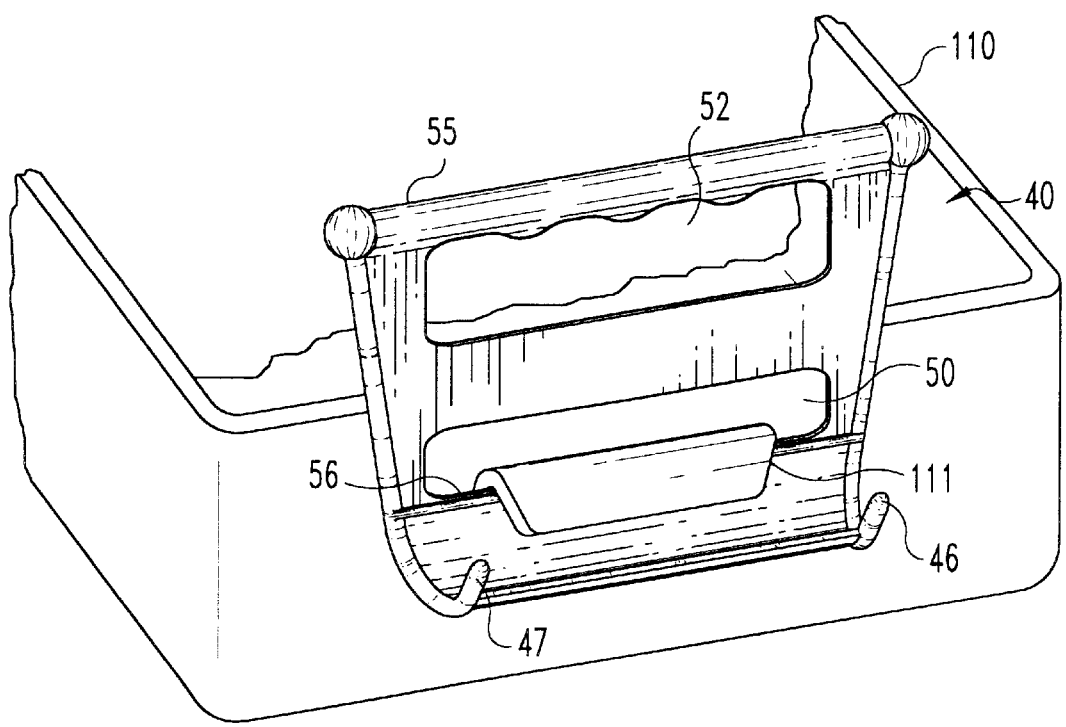
FIG. 14 is a partial perspective view of the tool shown in FIGS. 8–13 in position to lift a tray having hook handles.

In practice, the user needs a pair of tools 40, one in each hand for lifting each side of the tray. The tool 40 is versatile such that it can be used to lift trays having either loop handles or hook handles. As demonstrated in FIG. 14, in order to lift a tray 110 that has hook handles 111, the tool 40 is turned so that the first hook 46 and the second hook 47 face away from the tray 110. The user inserts the four fingers through the handhold slot 52 from the hook side towards the tray and holds on to the bar 55. Then the body 41 is pushed against the side of the tray so that the lip 56 of the opening 50 can be inserted under the book handle 111. The tool 40 is lifted until the hook handle 111 latches through the opening 50 to rest on the lower lip 56. Then the user lifts the tool 40 and thus the tray.

Figure 15:
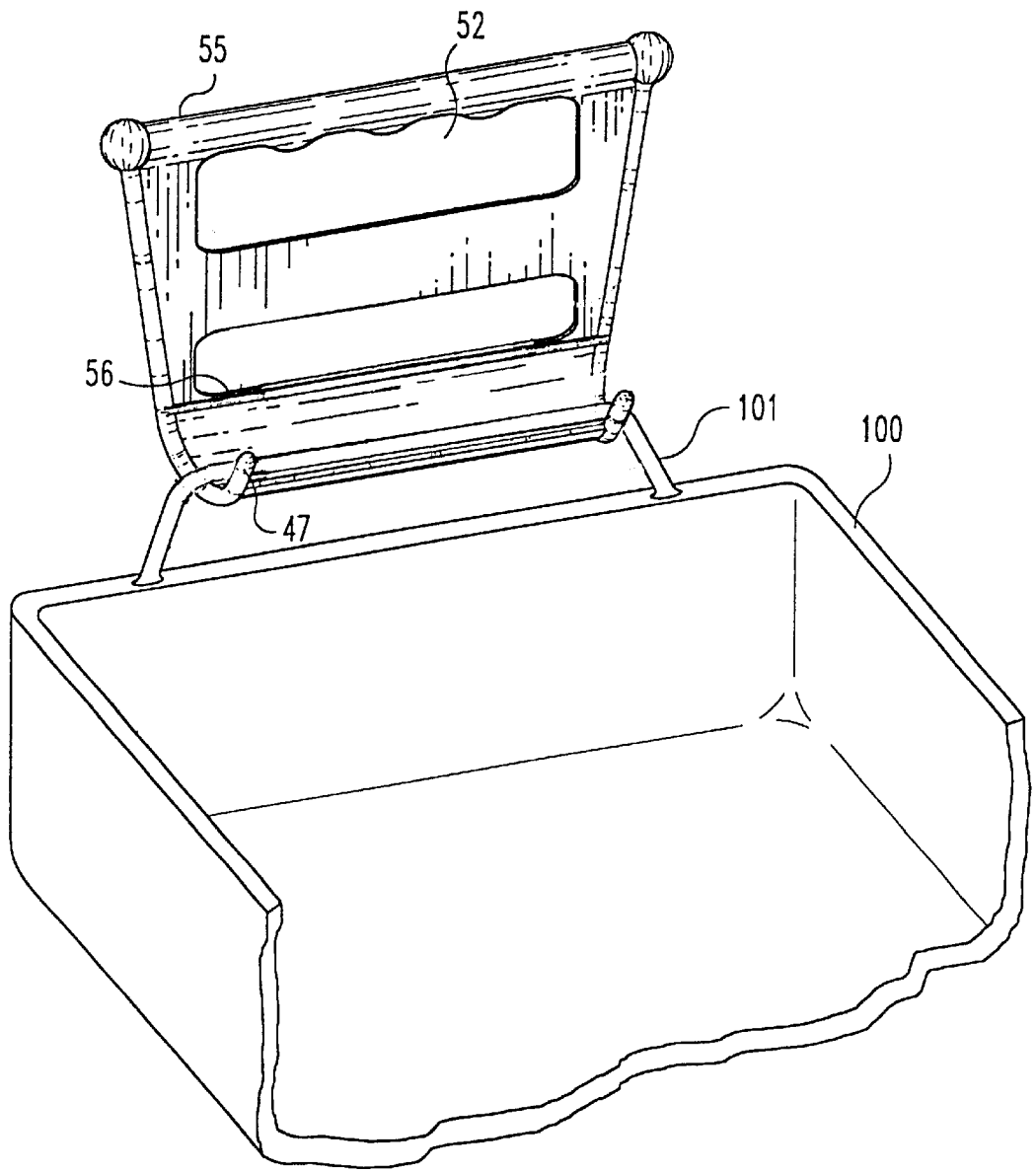
FIG. 15 is a partial perspective view of the tool shown in FIGS. 8–13 in position to lift a tray having loop handles.

With a tray having loop handles, the device 40 is held so that the first hook 46 and the second hook 47 face the loop handle. Thus, as shown in FIG. 15, the first hook 46 and the second hook 47 of each tool 40 are inserted through a loop handle 101 so that they catch the loop handle. The user uses each hand to grip the upper end 42 or inserts four fingers of each hand through the handhold slot 52 and holds the bar 55 to lift the tool 40 and the tray 100.

In another embodiment not shown, the tool comprises of a substantially planar body having an upper end and a lower end extending at a specific height. The body defines a first rim and a second rim extending between the upper end and the lower end. The body further defines an opening disposed close to the lower end for receiving a hook handle of a tray. In this embodiment, the body may have a handhold slot as describe for tool 10 and 40. With this embodiment, the tool can be used only with a tray having hook handles. Like the opening 50 described above, the opening of the instant embodiment defines a rigid lower lip which can be further supported by a rigid rib extending between the first rim and the second rim and immediately below the lip. The rigid rib supports the lower lip of the opening when the weight of the tray exerts a vertical force downwardly against the lower lip.

In all of the embodiments of the present invention, the tool may be made of any suitable material, preferably a tough, yet lightweight, plastic. The tool is preferably formed as single piece, such as in an injection molding process. Although not preferably, the present invention can be accomplished with a multi-piece tool. The body can be made as a solid piece or as a mesh, provided that the material is strong enough to hold the desired weight of the tray or the vessel including its contents.

For instance, the body 11 in FIG. 1 can be perforated to reduce material requirements. The tool of the present invention should withstand suitable methods of sterilization. Preferably, the tool is individually sterilized and wrapped prior to use, and should be disposed of after a single use.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A tool for lifting a tray having a loop handle, comprising:

a one-piece body including a substantially planar body portion having an upper end configured for handholding, a lower end opposite said upper end and opposite side edges between said upper and lower ends, said body defining a first rim and a second rim extending proximate a corresponding one of said opposite side edges between said upper end and said lower end, said first rim defining a first hook protruding from said lower end, said second rim defining a second hook protruding from said lower end, and said first and second hooks being separated by said lower end at a width whereby said first and second hooks are capable of being received by the loop handle of the tray.

2. The tool for lifting a tray according to claim 1 wherein said lower end includes a wide hook extending between said first hook and said second hook.

3. The tool for lifting a tray according to claim 1 wherein said body portion defines a handhold slot disposed below said upper end.

4. The tool for lifting a tray according to claim 3 wherein said upper end defines a support bar adjacent said handhold slot.

5. The tool for lifting a tray according to claim 4, wherein said support bar defines finger grip curves.

6. The tool for lifting a tray according to claim 1, wherein said first rim is defined along one of said side edges and said second rim is defined along the other of said side edges.

7. The tool for lifting a tray according to claim 4, wherein said body portion further defines an elongated opening, separate from said handhold slot, disposed above said lower end sized for receiving a hook handle of a tray.

8. The tool for lifting a tray according to claim 7 wherein said upper end defines a substantially rounded support bar for gripping.

9. The tool for lifting a tray according to claim 7 wherein said body defines a support rib immediately below said elongated opening for support.

10. The tool for lifting a tray according to claim 7 wherein said body is tapered such that said upper end is wider than said lower end.

11. A tool for lifting a tray having either loop handles or hook handles comprising:

a one-piece body including a substantially planar body portion having an upper end and a lower end, a first hook and a second hook protruding from said lower end, said first and second hooks being separated at said lower end at a width whereby said first and second hooks are capable of being received within a loop handle of the tray, and said body portion defining a handhold slot adjacent said upper end and a separate elongated opening disposed above said lower end configured for receiving a hook handle of the tray.

12. The tool for lifting a tray according to claim 11 wherein said upper end defines a support bar.

13. The tool for lifting a tray according to claim 11 wherein said body defines a support rib disposed immediately below said elongated opening.

14. The tool for lifting a tray according to claim 11 wherein:

said first and second hooks define a curvature; and said lower end defines a wide hook curving along the curvature of said first hook and said second hook.

15. The tool for lifting a tray according to claim 11 wherein said body is tapered such tat said upper end is wider than said lower end.

16. The tool for lifting a tray according to claim 11 wherein said body is made of disposable plastic.

17. The tool for lifting a tray according to claim 11, wherein:

said substantially planar body portion includes opposite side edges between said upper and lower ends; and further defines a first rim defined along one of said side edges and a second rim is defined along the other of said side edges.

* * * * *